(12) United States Patent
Madier-Vigneux et al.

(10) Patent No.: US 11,903,599 B2
(45) Date of Patent: Feb. 20, 2024

(54) COMPUTER-ASSISTED SHOULDER SURGERY AND METHOD

(71) Applicant: ORTHOSOFT ULC, Montreal (CA)

(72) Inventors: Joseph Madier-Vigneux, Montreal (CA); Karine Duval, Montreal (CA); Andreanne Goyette, Montreal (CA); Pablo Devanne Langlais, Montreal (CA); Kevin Miller, Montreal (CA); Michael Mueller, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 379 days.

(21) Appl. No.: 17/118,979

(22) Filed: Dec. 11, 2020

(65) Prior Publication Data

US 2021/0177441 A1  Jun. 17, 2021

Related U.S. Application Data

(60) Provisional application No. 63/027,653, filed on May 20, 2020, provisional application No. 62/947,295, filed on Dec. 12, 2019.

(51) Int. Cl.
| A61B 17/17 | (2006.01) |
| A61B 34/00 | (2016.01) |
| A61B 90/57 | (2016.01) |
| A61B 17/15 | (2006.01) |
| A61B 34/10 | (2016.01) |
| A61B 34/20 | (2016.01) |
| A61B 17/80 | (2006.01) |
| A61B 17/00 | (2006.01) |
| A61F 2/40  | (2006.01) |

(52) U.S. Cl.
CPC .......... *A61B 17/1778* (2016.11); *A61B 34/25* (2016.02); *A61B 90/57* (2016.02); *A61B 17/15* (2013.01); *A61B 17/8061* (2013.01); *A61B 2017/00991* (2013.01); *A61B 2034/104* (2016.02); *A61B 2034/2048* (2016.02); *A61F 2/4081* (2013.01)

(58) Field of Classification Search
CPC ................ A61B 17/1778; A61B 17/15; A61B 2034/2048; A61B 17/8061; A61B 34/25; A61B 90/57; A61B 2034/104; A61B 2017/00991; A61B 2/4081
See application file for complete search history.

(56) References Cited

U.S. PATENT DOCUMENTS

2009/0270864 A1* 10/2009 Poncet ...................... A61F 2/40
                                                      606/83
2014/0031672 A1*  1/2014 McCaulley ............ A61B 34/20
                                                      600/424

(Continued)

*Primary Examiner* — Kevin T Truong
*Assistant Examiner* — Diana Jones
(74) *Attorney, Agent, or Firm* — NORTON ROSE FULBRIGHT CANADA LLP

(57) ABSTRACT

A humerus cutting assembly includes a guide frame having an attachment member adapted to be secured to a humerus adjacent to a humeral head. A cutting guide is releasably connected to the guide frame, the cutting guide configured to guide a tool in altering the humeral head. One or more inertial sensor units is on the cutting guide, the inertial sensor unit tracking an orientation of the cutting guide relative to the humerus based on the releasable connection between the cutting guide and the guide frame.

17 Claims, 10 Drawing Sheets

(56) References Cited

U.S. PATENT DOCUMENTS

2015/0320430 A1* 11/2015 Kehres .................. A61B 17/15
  606/87
2016/0374697 A1* 12/2016 Kehres .................. A61B 17/15
  606/87
2017/0100132 A1* 4/2017 Collazo ................. A61B 17/15
2018/0116758 A1 5/2018 Schlosser et al.
2018/0353192 A1* 12/2018 Leveille ............. A61B 17/1764

* cited by examiner

COMPUTER-ASSISTED SHOULDER SURGERY AND METHOD

CROSS-REFERENCE TO RELATED APPLICATION

The application claims the priorities of U.S. Patent Application No. 62/947,295, filed on Dec. 12, 2019, and U.S. Patent Application No. 63/027,653, filed on May 20, 2020, both of which are incorporated herein by reference.

TECHNICAL FIELD

The application relates generally to computer-assisted surgery of the type used in shoulder surgery involving the humerus and/or the scapula.

BACKGROUND OF THE ART

In computer-assisted surgery (CAS) systems which employ inertial-based or micro-electro-mechanical sensor (MEMS), trackable members continue to be developed. One of the principal steps in navigating a bone with inertial sensors is to determine a coordinate system of the bone relative to the sensors, so as to be able to determine the orientation of the bone. For the humerus, the orientation of the bone may be expressed in terms of retroversion and inclination, relative to anatomical axis of the humerus. In contrast, navigation of the scapula may rely on preoperative planning or on physical landmarks, due to the thinness of the bone.

There remains a need for improved surgical tools which may be used in conjunction with a CAS system in order to digitally navigate a surgical cut of a humerus and/or position an implant on a glenoid.

SUMMARY

In one aspect, there is provided a humerus cutting assembly comprising: a guide frame having an attachment member adapted to be secured to a humerus adjacent to a humeral head, and a cutting guide releasably connected to the guide frame, the cutting guide configured to guide a tool in altering the humeral head; at least one inertial sensor unit on the cutting guide, the inertial sensor unit tracking an orientation of the cutting guide relative to the humerus based on the releasable connection between the cutting guide and the guide frame.

In another aspect, there is provided a system for guiding an alteration to a head of a humerus comprising: a processor unit, and a non-transitory computer-readable memory communicatively coupled to the processor and comprising computer-readable program instructions executable by the processor unit for: setting a reference orientation of a humerus when an assembly featuring a cutting guide is attached to the humerus in a given orientation, obtaining an output from at least one inertial sensor on the cutting guide as an orientation of the cutting guide relative to the humerus is varied, tracking a current orientation of the humerus relative to the reference orientation using the output, and calculating and outputting at least one angle being indicative of an alteration to the head of the humerus associated to the current orientation of the cutting guide.

In a further aspect, there is provided a glenoid navigation assembly comprising: a pin guide having a cannulated shaft, the cannulated shaft adapted to receive a guide pin therein; a registration interface at the end of the cannulated shaft and configured for abutting a glenoid, the registration interface having at least one visual alignment member for visually assisting in a positioning of the guide pin on the glenoid; and at least one inertial sensor unit on the glenoid navigation assembly, the inertial sensor unit tracking an orientation of the cannulated shaft relative to the glenoid based on a contact between the registration interface and the glenoid surface.

In a still further aspect, there is provided a system for guiding an alteration to a glenoid comprising: a processor unit, and a non-transitory computer-readable memory communicatively coupled to the processor and comprising computer-readable program instructions executable by the processor unit for: setting a reference orientation of a glenoid when an assembly featuring a guide is applied against the glenoid at a given position, obtaining an output from an inertial sensor on the guide as an orientation of the guide relative to the glenoid is varied, tracking a current orientation of the guide relative to the reference orientation using the output, and calculating and outputting an angle, the angle being indicative of an alteration to the glenoid associated to the current orientation of the guide.

In a still further aspect, there is provided a system for guiding an alteration to a head of a humerus comprising: a processor unit, and a non-transitory computer-readable memory communicatively coupled to the processor and comprising computer-readable program instructions executable by the processor unit for: setting a reference orientation of a humerus when an assembly featuring a cutting guide is attached to the humerus in a predetermined manner, robotically manipulating the guide relative to the humerus with a robotic arm, obtaining an output representative of a current orientation of the guide as the guide is robotically manipulated, tracking a current orientation of the humerus relative to the reference orientation using the output, calculating and outputting at least one angle being indicative of an alteration to the head of the humerus associated to the current orientation of the cutting guide, and auto-blocking the robotic arm when a desired value for the angle is reached.

In a still further aspect, there is provided a system for guiding an alteration to a glenoid comprising: a processor unit, and a non-transitory computer-readable memory communicatively coupled to the processor and comprising computer-readable program instructions executable by the processor unit for: setting a reference orientation of a glenoid when an assembly featuring a guide is applied against the glenoid in a given position, robotically manipulating the guide relative to the glenoid with a robotic arm, obtaining an output representative of a current orientation of the guide as the guide is robotically manipulated, tracking a current orientation of the guide relative to the reference orientation using the output, calculating and outputting at least one angle being indicative of an alteration to the glenoid associated to the current orientation of the guide, and auto-blocking the robotic arm when a desired value for the angle is reached.

DESCRIPTION OF THE DRAWINGS

Reference is now made to the accompanying figures in which.

DETAILED DESCRIPTION

Figure 1:
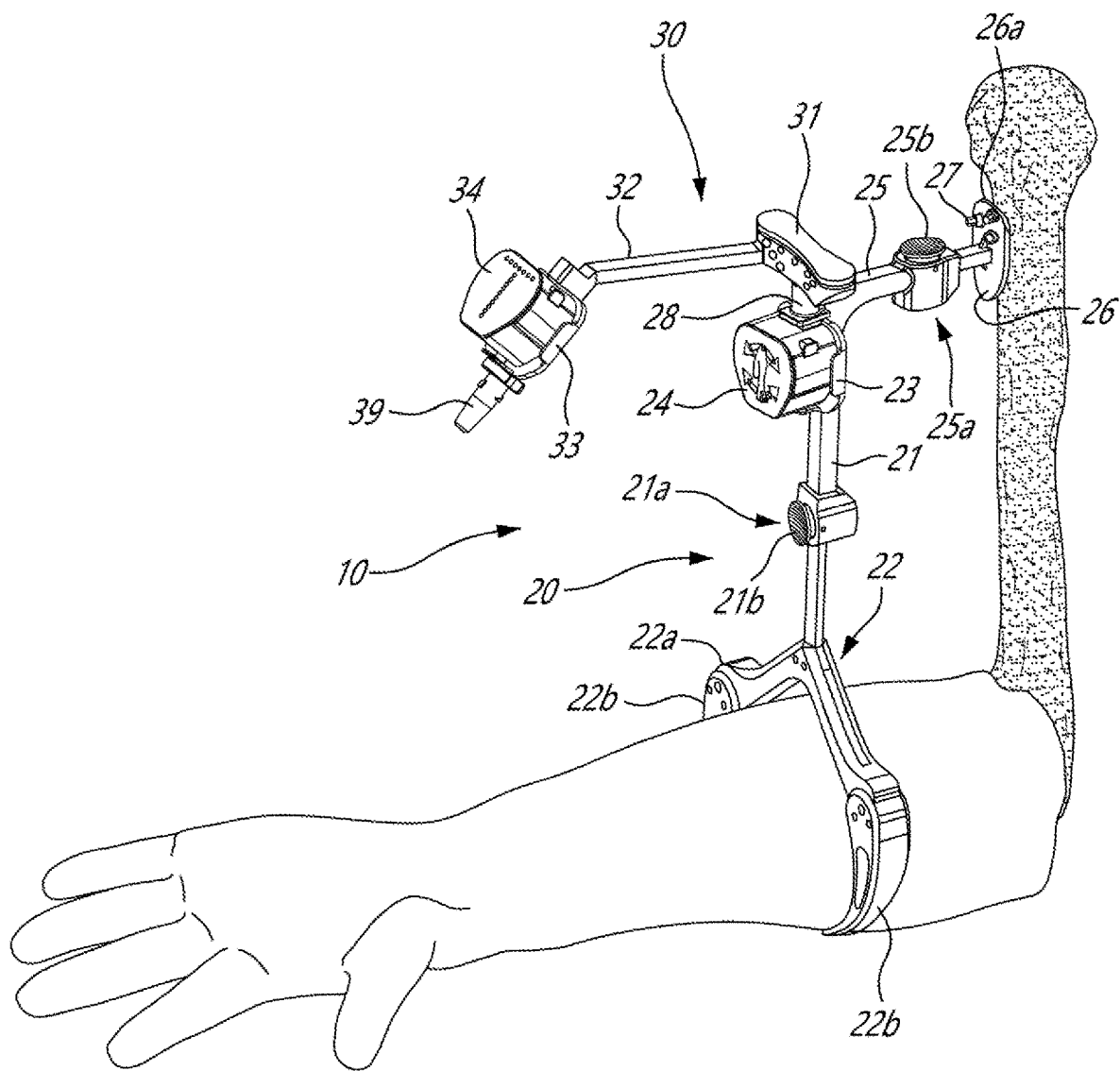
FIG. 1 is a perspective view of a humerus cutting assembly in accordance with the present disclosure.

Referring to the drawings and more particularly to FIGS. 1-5, a humerus cutting assembly in accordance with the present disclosure is generally shown at 10 as positioned on an arm of a user. The arm of the user is shown schematically with the humerus fully exposed, but in an operative setting, only a limited portion of the humerus may be exposed, i.e., at the shoulder joint, with a limited part of the glenoid exposed. The humerus cutting assembly 10 is of the type that may be used to assist in altering the humeral head. In an embodiment, the humerus cutting assembly 10 is used to cut a plane on the humeral head, for instance in the context of glenoid surgery or reverse glenoid surgery. The humerus cutting assembly 10 may be used for different operations as well. The plane of resection on the humeral head is typically oriented to a desired retroversion and/or inclination. These angle values may be relative to an anatomical axis of the humerus that extends along the length of the humerus. Retroversion, a.k.a., retroversion angle, may be defined as being a projection of a normal of the resection plane onto a transverse plane of the humerus, relative to a medio-lateral axis. Inclination, a.k.a., inclination angle, may be defined as a projection of a normal of the resection plane onto the frontal plane of the humerus, relative to the anatomical axis of the humerus. Other or different angles may also come into consideration when planning and performing a cut on the humeral head.

The humerus cutting assembly 10 may have a guide frame 20 and a cutting guide 30. The frame 20 and guide 30 are described as two components (or groups of components) for clarity, but they may be viewed as a single group of components, or more than two components as well. The guide frame 20 is used to form a structural reference for the cutting guide 30 and/or assist in defining a reference coordinate system, a.k.a., frame of reference. The guide frame 20 may for instance be attached to the arm of a patient in a given orientation, such as being generally parallel to the anatomical axis of the humerus. The cutting guide 30 is used to guide alteration tools, such as a flat saw blade, in the manner configured in the illustrated embodiment. Other cutting implements or guides could be used, such as a drill guide for a drill among possible tools. Other tools may include a reamer, etc.

Figure 2:
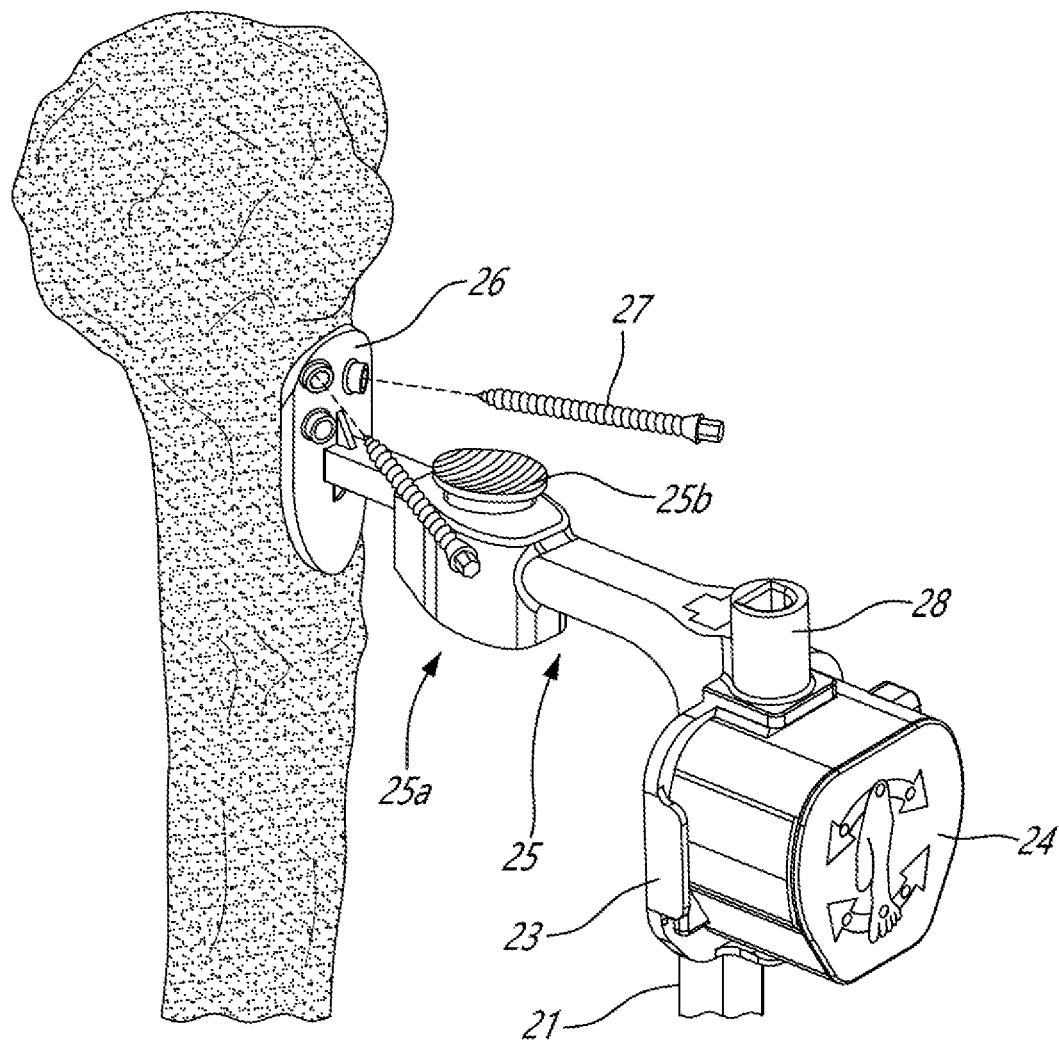
FIG. 2 is a perspective view of a guide frame of the humerus cutting assembly of FIG. 1.
Figure 3:
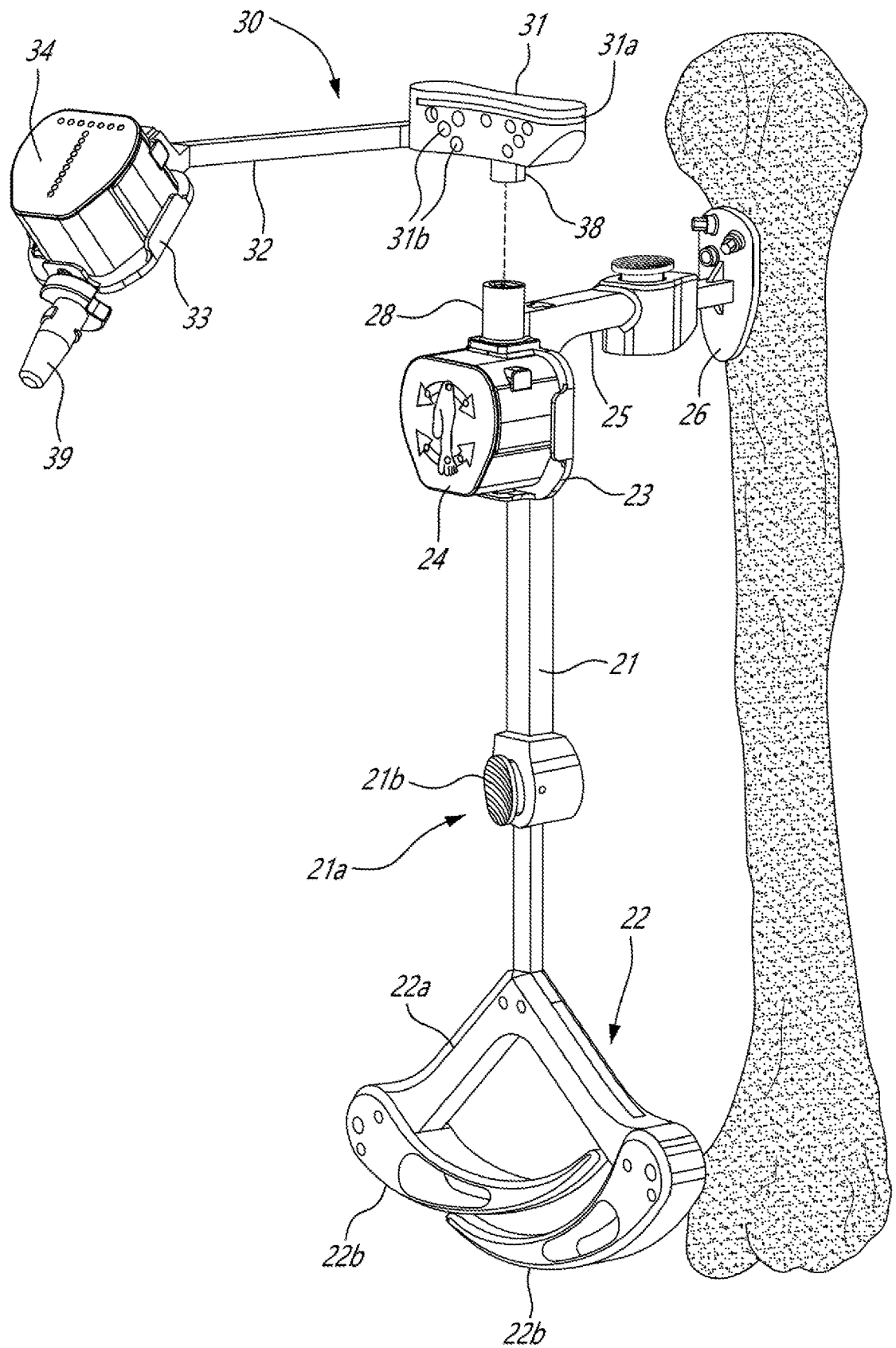
FIG. 3 is an assembly view of the humerus cutting assembly of FIG. 1.

Referring to FIGS. 1 to 3, the guide frame 20 is shown as having a main arm 21. AS a possibility, the main arm 21 extends generally parallel to the humerus when installed onto the arm of the patient. The main arm 21 may have a translational joint so as to expand or contract to adapt the guide frame 20 to the user's arm length. In an embodiment, the translational expansion may be possible by a telescopic joint 21a. As another option, the main arm 21 ha a cylindrical joint enabling a translation and a rotation. In an embodiment, the telescopic joint 21a defines a plurality of indexed positions with appropriate snap-fit indexing features (e.g., spring loaded ball and groove). Other joint configurations may be used, such as endless screw engagement, set screw locking, and/or biasing force to block the movement of the segments of the main arm 21. As shown, a push button or detent 21b may be present to release the lock of the arm portions and allow expansion or contraction of the main arm 21. The main arm 21 may maintain a desired length by such self-blocking features at the telescopic joint 21a.

A clamp 22 may be located at a bottom end of the main arm 21. The clamp 22 may be provided to non-invasively attach and fix the guide frame 20 to a user's forearm, for example. In another embodiment, the clamp 22 could be used to attach the guide frame 20 to a lower part of the humerus. Other configurations are contemplated. In an embodiment, the clamp 22 has an inverted V frame 22a at the end of which are positioned jaws 22b. The jaws 22b may be pivotally connected to the V frame 22a. As shown, the jaws 22b may be curved inwardly so as to emulate the generally circular shape of the forearm or of the upper arm near the elbow joint. In an embodiment, the jaws 22b are biased toward one another so as to naturally exert pressure and clamp onto the forearm. Other configurations are considered as well. If the jaws 22b are biased, the biasing force should be sufficient to allow a suitable clamping force while not preventing the jaws 22b from being manually separated from one another. In an embodiment, the clamp 22 is relatively symmetric to allow the self-centering of the clamp 22 on the portion of the arm it will grasp.

Other bottom end configurations may be present on the guide frame 20. For example, as an alternative to the jaws, it is considered to provide a strap, an elastic, and/or an U-shaped structure or the like, located at the bottom end of the main arm 21 or at the end of the V frame 22a. Therefore, when positioning the guide frame 20 on the arm, the position of the lower part of the guide frame 20 can readily be adjusted by manipulations of the jaws 22b or equivalent. Such configurations are non-invasive as they attach to the surface of the skin, but invasive attachments are considered as well.

A support 23 may be provided on the main arm 21 or on any other portion of the guide frame 20, the support 23 being configured to receive an inertial sensor unit 24 thereon, as one of the possible types of tracking technologies that may be used with the guide frame 20. In an embodiment, the inertial sensor unit 24 is in the form of a pod that is releasably connectable to the support 23. The inertial sensor unit 24 may include a processor and a non-transitory computer-readable memory communicatively coupled to the processor and comprising computer-readable program instructions executable by the processor. Moreover, as seen in the figures, the inertial sensor unit 24 may be self-contained, in that it is precalibrated for operation, has its own powering or may be connected to a power source, and has an interface, such as in the form of a display thereon (e.g., LED indicators). Hence, the humerus cutting assembly 10 may be qualified as being a computer-assisted solution by the presence of the inertial sensor unit(s) 24 alone. It is also considered to have a computerized ecosystem including the inertial sensor unit(s) 24, a monitor, another processing unit, a tablet or like portable hand-held device, etc.

The inertial sensor unit 24 may also be directly integrated onto the guide frame 20, though the releasable configuration may be well suited for preprogramming, sterilization, etc. As the main arm 21 may preferably be oriented in a generally parallel manner to the anatomical axis of the humerus, the positioning of the support 23 on the main arm 21 may facilitate the calibrating of the inertial sensor unit 24. In an embodiment, the interconnection between the support 23 and the inertial sensor unit 24 is such that it is calibrated into the inertial sensor unit 24. Stated differently, once the inertial sensor unit 24 is in the support 23, the inertial sensor unit 24 may have been pre-calibrated in such a way that a coordinate system maintained and tracked by the inertial sensor unit 24 thereof is aligned with a length of the main arm 21. Accordingly, if the main arm 21 is generally parallel to the humerus anatomical axis, the inertial sensor unit 24 may automatically track the anatomical axis of the humerus in its XYZ coordinate system. Therefore, in an embodiment, once the inertial sensor unit 24 is turned on, with the guide frame 20 attached to the arm, the inertial sensor unit 24 may continuously track an orientation of the upper arm, in phi, theta, rho (i.e., three rotational degrees of freedom—DOF).

Referring to FIG. 2, a side arm 25 may project from the main arm 21. In an embodiment, the side arm 25 is perpendicular or transverse to the main arm 21. The side arm 25 may also have a telescopic joint, shown as 25a, with a push button 25b. The configuration of the telescopic joint 25a may be as described above for the telescopic joint 21a, with the possibility of forming a self-blocking joint. It is also contemplated to have the side arm 25 be of fixed length as well. An attachment plate 26, or like attachment member, is located at an end of the side arm 25. The attachment plate 26 is of the type that will abut against the bone. In an embodiment, the attachment plate 26 may be provided with a patient-specific contour being the result of pre-operative modelling of the humerus, for the attachment plate 26 to be seated in an unique complementary manner against a pre-defined portion of the humerus. The patient-specific surfacing of the attachment plate 26 may be known as being a negative contour of the bone portion. The predictability of the patient-specific contour may contribute to the pre-calibration of the inertial sensor unit 24. The patient-specific contour is optional as the attachment plate 26 may be a stock plate not specifically designed with the user's anatomical model. The attachment plate 26 has attachment holes 26a by which fasteners 27 may be used to secure the attachment plate 26 and therefore the guide frame 20 to the humerus. Fasteners 27 may be screws, for example. Straps may be an alternative to screws. The holes 26a may be oriented for the fasteners 27 to converge into the bone.

Figure 4:
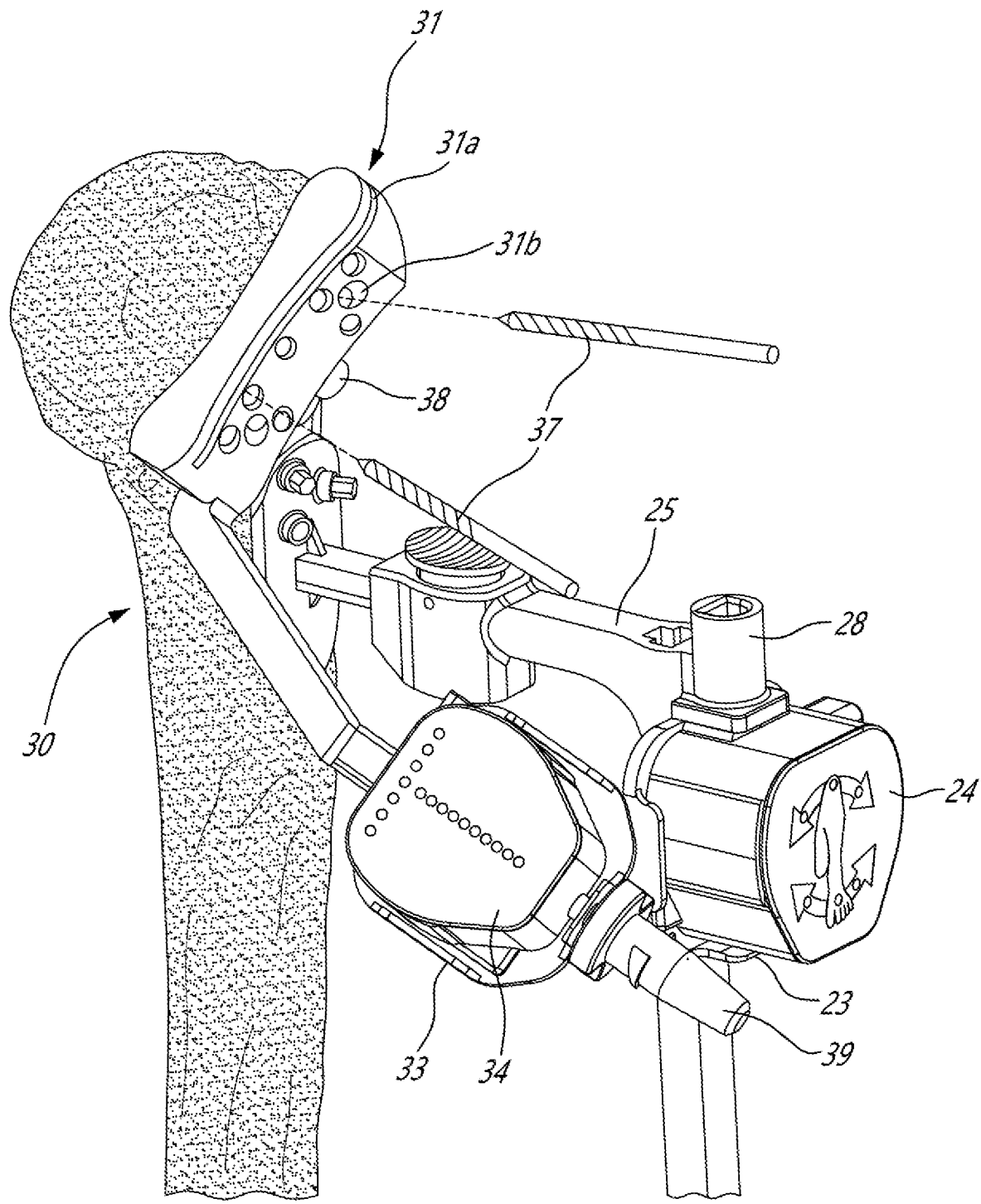
FIG. 4 is a perspective view showing a relation between a cutting guide and the guide frame of the humerus cutting assembly of FIG. 1, during positioning of the cutting guide on the humerus.

Therefore, as shown in FIGS. 3 and 4, the guide frame 20 may be rigidly connected to the humerus, with a position of the lower portion of the guide frame 20 being readily adjustable, for instance to achieve a visual parallel relation between the main arm 21 and the upper arm, though this is only an option. A connector 28 may be integral with the main arm 21 or other portions of the guide frame 20. In an embodiment, the connector 28 is in a fixed relation with respect to the inertial sensor unit 24. The connector 28 may have any appropriate shape or configuration. In an embodiment, the connector 28 is a tube having a receptacle. As observed, the receptacle has a non-circular rotation. Stated differently, once a complementary connector is received in the connector 28, rotation is precluded by the non-circular shape of the connector 28. Any appropriate anti-rotation feature may be used, and ensure a fixed orientation of a component connected to the guide frame 20 via the connector 28.

Figure 5:
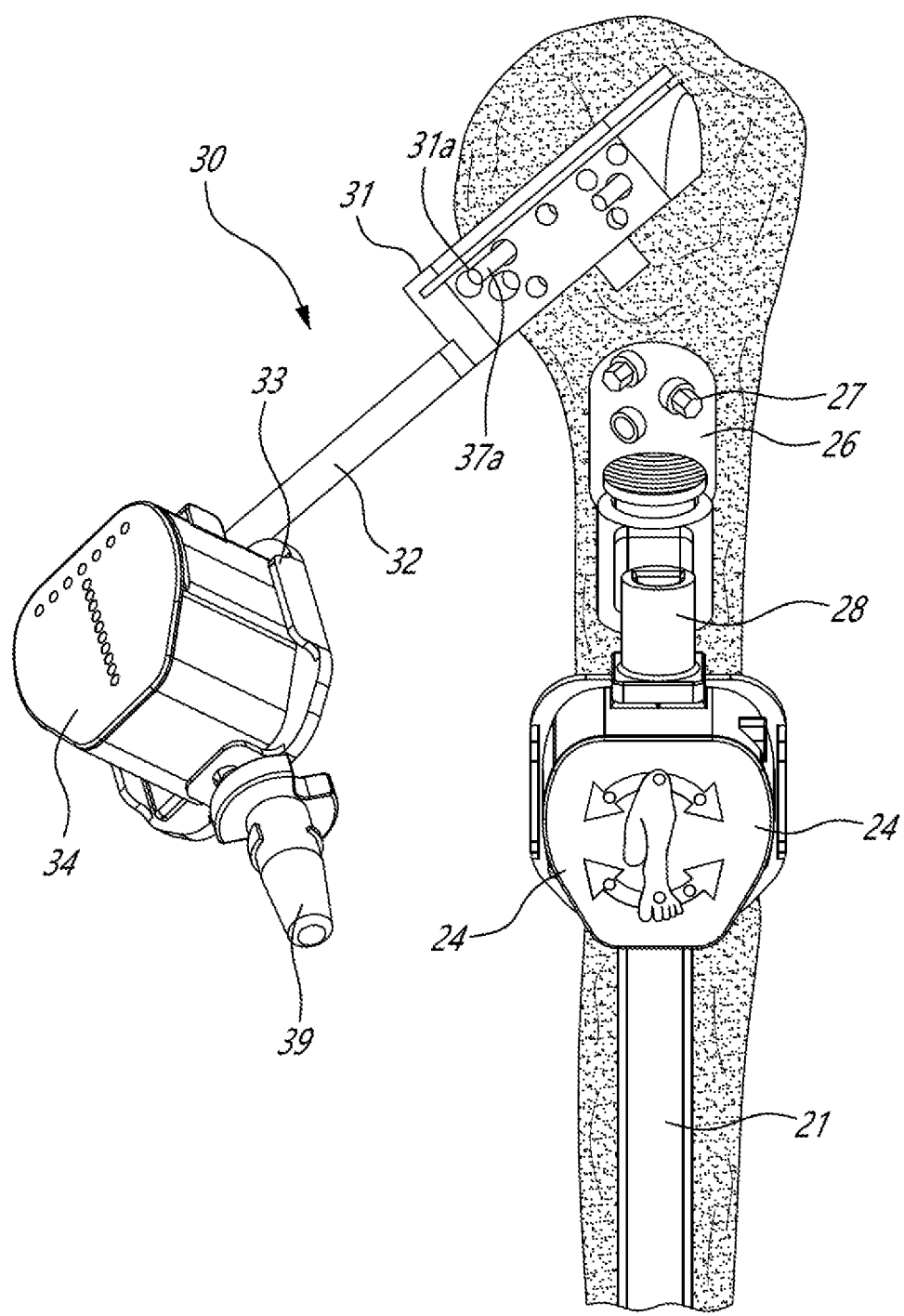
FIG. 5 is a perspective view of the humerus cutting assembly as positioned for performing a resection of the humeral head.

Referring to FIGS. 3 and 5, the cutting guide 30 is shown as having a cutting block 31. The cutting block 31 is of the type that defines a cutting slot 31a sized so as to receive a saw blade therein, in accordance with an embodiment. Holes 31b may also be defined in the cutting block 31 so as to secure the cutting guide 30 via the cutting block 31 to the humeral head or in proximity thereof, as shown in FIGS. 4 and 5. The humerus cutting assembly 10 is shown as being of the type used to define a cutting plane on the humeral head but other cutting implements may be used instead of the cutting guide 30.

An arm 32 may project from the cutting block 31 and has a support 33 at its end. The support 33 is similar to the support 23 and may therefore be shaped to receive a tracker device such as another inertial sensor 34. Again, the complementary coupling of the inertial sensor unit 34 and the support 33 allows the initialization of the inertial sensor unit 34 to be in a calibrated arrangement with the cutting guide 30 and more particularly with the cutting slot 31a. Stated differently, once the inertial sensor unit 34 is in the support 33 and is turned on, the inertial sensor unit 34 may track the location in space of the plane of the cutting slot 31a through its readings. Fasteners 37 (e.g., screws, pins) may be used in conjunction with the cutting guide 30 and into the cutting holes 31b so as to secure the cutting guide 30 to the humerus in the manner shown in FIG. 5. A connector 38 is part of the cutting guide 30. In an embodiment, the connector 38 is a pin, nipple, coupler or the like that has a shape complementary to that of the connector 28 for complementary male-female coupling, that may provide a unique coupling orientation. The unique coupling orientation may be defined as a single possible orientation of the cutting guide 30 when coupled to the guide frame 20 when the pair is interconnected via the releasable connection. The reverse arrangement is possible as well (female at 38, male at 28), as are other complementary couplers.

The inertial sensor units 24 and 34 are preprogrammed, taking into consideration the geometrical relation between the guide frame 20 and the cutting guide 30, such that when the cutting guide 30 is coupled to the guide frame 20 in the manner shown in FIG. 1, the inertial sensor units 24 and 34 may perform a handshake such that a subsequent movement of the cutting guide 30 as detached from the guide frame 20 is tracked at least in orientation, relative to the frame of reference of the humerus, i.e., the anatomical axis of the humerus tracked by the inertial sensor unit 24 as described above. For this reason, the coupling between the connector 38 and the connector 28 is complementary and unique. Therefore, once this handshake is done, the cutting guide 30 is navigated via its inertial sensor unit 34, e.g., using a dead reckoning tracking technique, such that it may be positioned in the manner shown in FIGS. 4 and 5, relative to the virtual reference system of the humerus. In doing so, desired retroversion and inclination values may be attained. If the humerus moves, the inertial sensor unit 24 secured thereon may track its movements for such movement to be compensated for. In an embodiment, the retroversion and inclination values have been preplanned and/or may be output by the inertial sensor unit 24 and/or 34. In another embodiment, a single inertial sensor unit 24 is used, and this may require that the humerus be constrained from moving. The single inertial sensor unit 24 may set the virtual reference system for the humerus, including the anatomical axis. The virtual reference system may include other axes, a transverse and a frontal plane of the humerus. If a single inertial sensor unit is used, the inertial sensor unit 24 may be detached from the support 23 and attached to the support 33 in the cutting guide 30, while the arm is fixed and the guide frame 20 and cutting guide 30 being in a known geometrical relation, e.g., via the complementary coupling of the connectors 28 and 38. A dead reckoning tracking technique is used during the transfer of the inertial sensor unit 24 from the support 23 to the support 33, such that the orientation of the virtual reference system of the humerus is preserved. The cutting guide 30 may be detached from the guide frame 20, and is tracked relative to the fixed humerus, using dead reckoning tracking technique, for the retroversion and inclination values to be calculated and output in real-time by the inertial sensor unit 24, or 34.

Figure 11:
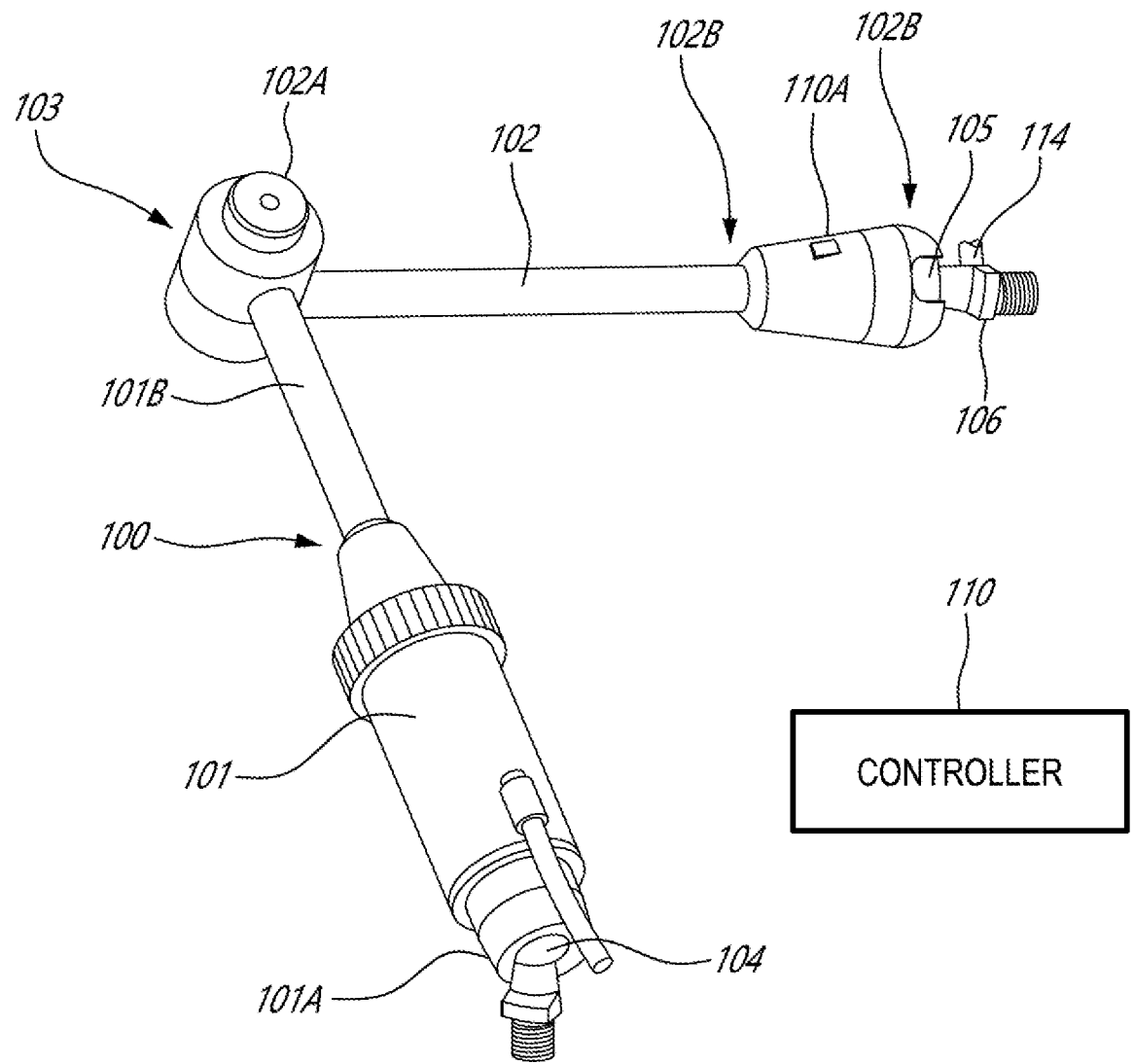
FIG. 11 is a perspective view of a robotic arm that may be used with humerus cutting assembly of FIG. 1 and/or the glenoid navigation assembly of FIG. 7.

The movements of the cutting guide 30 may be effected using a robotic arm such as the one shown at 100 in FIG. 11. The cutting guide 30 may therefore have a coupler 39 thereon for being connected to the robotic arm 100. The coupler 39 may have any appropriate configuration. The robotic arm 100 of FIG. 11 may be suited to maintain a desired orientation of the cutting guide 30 while it is drilled to the humerus, as a possibility. If the humerus is fixed, the robotic arm 100 may maintain a desired orientation of the cutting guide 30 without the use of the fasteners 37, as a possibility.

Although the guide frame 20 and the cutting guide 30 are shown as being separable components, it is contemplated to have these components interconnected by a mechanism as well, for instance through the bone altering.

Figure 6:
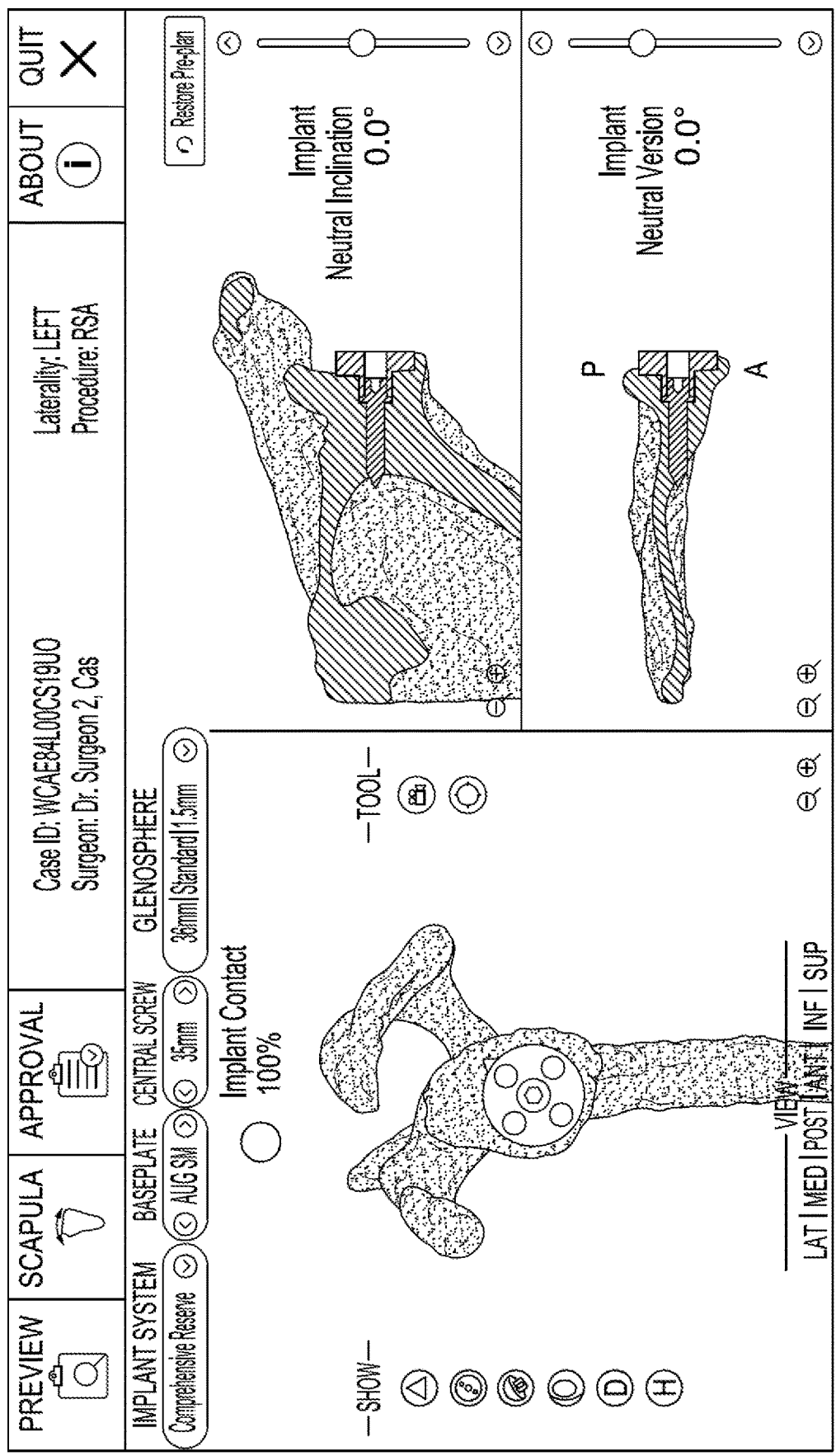
FIG. 6 is a graphic user interface showing virtual navigation of a glenoid implant model in inclination and version in preoperative planning.

Referring now to FIG. 6, there is illustrated a graphic user interface (GUI) showing a scapula with a virtual model of an implant thereon. The scapula may for example be a virtual model of the patient's scapula obtained from imaging such as CT or MRI, or the combination of imaging and other techniques, such as 2D to 3D X-Ray images, with a merge to a generic scapula from a bone atlas. As observed from the right-hand side, the positioning of the fastener in the glenoid is strategic considering that the scapula is relatively thin. A functionality of the present disclosure is to locate the implant in such a way that the fastener does not pierce through the hidden side of the scapula. For example, the position of the fastener may be determined as a function of depth, whereas the orientation of the trajectory of the fastener is defined in terms of inclination and version. The inclination, a.k.a., inclination angle, may be the projection of the axis of the fastener onto the frontal plane, relative to the mediolateral axis. The version, a.k.a., the version angle, may be defined as the projection of the fastener axis on the transverse plane, relative to the mediolateral axis. Other angles may be monitored.

The GUI of FIG. 6 may help a surgeon or other operator in planning a desired trajectory for the fastener. Therefore, the data input into the GUI in FIG. 6, for instance in the form of a virtual movement of the model of the implant on the scapula, may serve in a planning stage occurring preoperatively. Thereafter, a glenoid navigation assembly, as shown as 50 in FIGS. 7 to 10, may be used to replicate the planned position and orientation (i.e., trajectory) of the fastener or implant (e.g., implant peg). However, the glenoid navigation assembly may also be used without any pre-planning.

Figure 7:
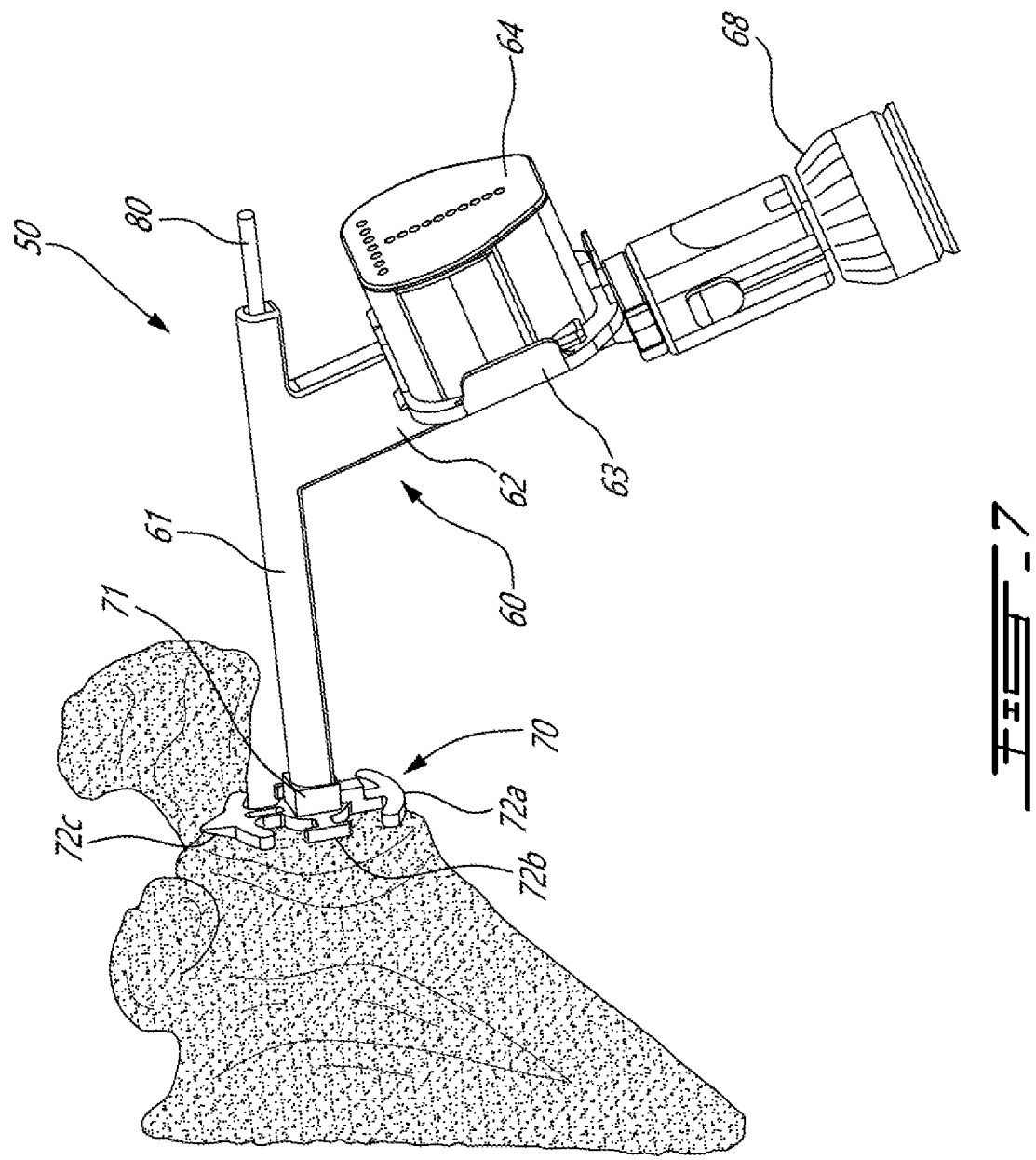
FIG. 7 is a perspective view of a glenoid navigation assembly in accordance with the present disclosure.

Referring to FIG. 7, the glenoid navigation assembly 50 is shown having a pin guide 60, a registration interface 70 and a pin 80. In an embodiment, the pin guide 60 and the registration interface 70 are available as a kit and separately from the pin 80 which may not be part of the glenoid navigation assembly 50. In an embodiment, the pin 80 is stock in that it may not be specifically designed to be used with the glenoid navigation assembly 50.

The pin guide 60 has an elongated cannulated shaft 61. The cannulated shaft 61 therefore has an internal channel through which the pin 80 may slide in at least one translational DOF—together the elongated cannulated shaft 61 and the pin 80 form a cylindrical joint. As observed from FIG. 9, the cannulated shaft 61 may have a tapered end 61a to facilitate its movement against the glenoid, for instance by limiting a contact surface between the shaft 61 and the glenoid. A handle 62, or any other coupler, may project generally laterally from the cannulated shaft 61. The handle 62 may be used to maneuver the pin guide 60. A support 63 with inertial sensor unit 64 may be positioned on any part of the pin guide 60 though it may conveniently be positioned on the handle 62. The set of support 63 and inertial sensor unit 64 is generally as described above for the humerus cutting assembly 10 in the form of the supports 23 and 33 in the inertial sensor units 24 and 34. As described for the humerus cutting assembly 10, the inertial sensor unit 64 may be self-contained and/or may also be connected directly to the handle 62, etc. The inertial sensor unit 64 may therefore be in a precise location on the pin guide 60 such that, when turned on, the inertial sensor unit 64 may continuously track the orientation of the cannulated shaft 61. Therefore, once initialized, it is possible to track an orientation of the cannulated shaft 61 and pin 80 therein in a coordinate system of the inertial sensor unit 64. The tracking may be in three rotational DOFs. A connector 68 may be at an end of the handle 62 for connection to the robotic arm 100 of FIG. 11, according to an embodiment, through the glenoid navigation assembly 50 may be operated in a free hand mode as well. It is also observed that the cannulated shaft 61 may have a non-circular cross-section on its outer surface, or like anti rotation feature.

Figure 8:
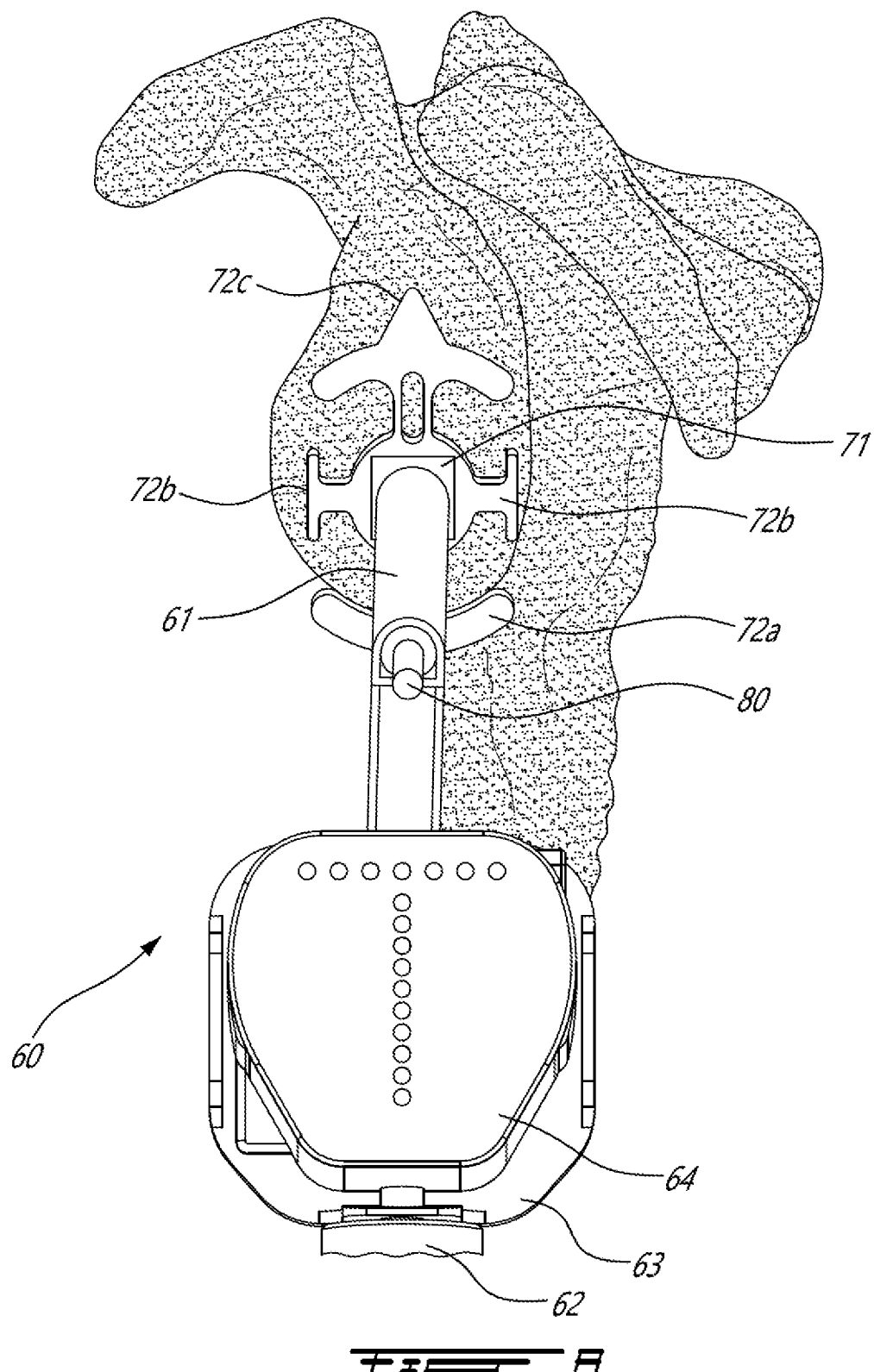
FIG. 8 is a lateral view of the glenoid navigation assembly.

As observed from FIG. 7, the glenoid navigation assembly 50 may be moved relative to the scapula so as to position the pin 80 in a desired position and orientation in the glenoid. Referring to FIGS. 7 and 8, the registration interface 70 is at the end of the cannulated shaft 61 of the pin guide 60. Therefore, when the glenoid navigation assembly 50 is positioned against the glenoid as in FIG. 7, the registration interface 70 may be in contact with the glenoid. The registration interface 70 may be patient-specific in that it may be shaped as a function of the patient-specific bone geometry. This may be done for instance using negative contouring, with a virtual model of the bone. In another embodiment, the registration interface 70 is not patient-specific. The registration interface 70 may come in different sizes depending on the patient's bone size, and the selection of the registration interface 70 may be guided by preoperative imaging or in situ sighting. The registration interface 70 is a visual indicator to assist an operator, such as a surgeon, in positioning the pin 80 in the glenoid.

As illustrated, the registration interface 70 has a joint portion 71 that may be generally centralized within the registration interface 70. The joint portion 71 may be defined by a bore 71a that has a shape complementary to that of the cannulated shaft 61 of the pin guide 60. Therefore, once the registration interface 70 is mounted to the cannulated shaft 61, the registration interface 70 may slide along an outer surface of the cannulated shaft 61. As mentioned above, the cannulated shaft 61 has a non-circular cross-section, or like anti-rotation feature, such that the only degree of freedom between the registration interface 70 and the pin guide 60 is a translation, though other embodiments are considered. It is also possible to lock the registration interface 70 at the end of the cannulated shaft 61 of the pin guide 60. Any appropriate locking feature may be provided therefor, including for example a set screw.

Referring to FIGS. 7 and 8, the registration interface 70 may have different alignment member(s) 72, for providing visual alignment. As an example, the alignment members 72 may include arcs 72a at the bottom and at the top of the registration interface 70. The arcs 72a may be spaced apart by a distance corresponding to the size of the glenoid, or of an implant (e.g., glenosphere). It is also contemplated to use abutments such that the arcs 72a may abut against, for example, a rim of the glenoid. Wings 72b may also be present and may be used to assist in spacing the registration interface 70 from sides of the glenoid. For example, the registration interface 70 may be positioned so as to have one of the wings 72b aligned with the periphery of the glenoid. As another possible alignment member 72, a pointer 72c may project from a remainder of the registration interface 70. The pointer 72c may be aligned with a vertical axis or towards any anatomical feature of the scapula that may be seen, such as the coracoid process. One or more of 72a, 72b 72c may be present in the alignment member 72. Therefore, in the manner shown in FIG. 8, the registration interface 70 may be used to place the pin guide 60 in an appropriate location such as a pre-operatively planned position.

Figure 9:
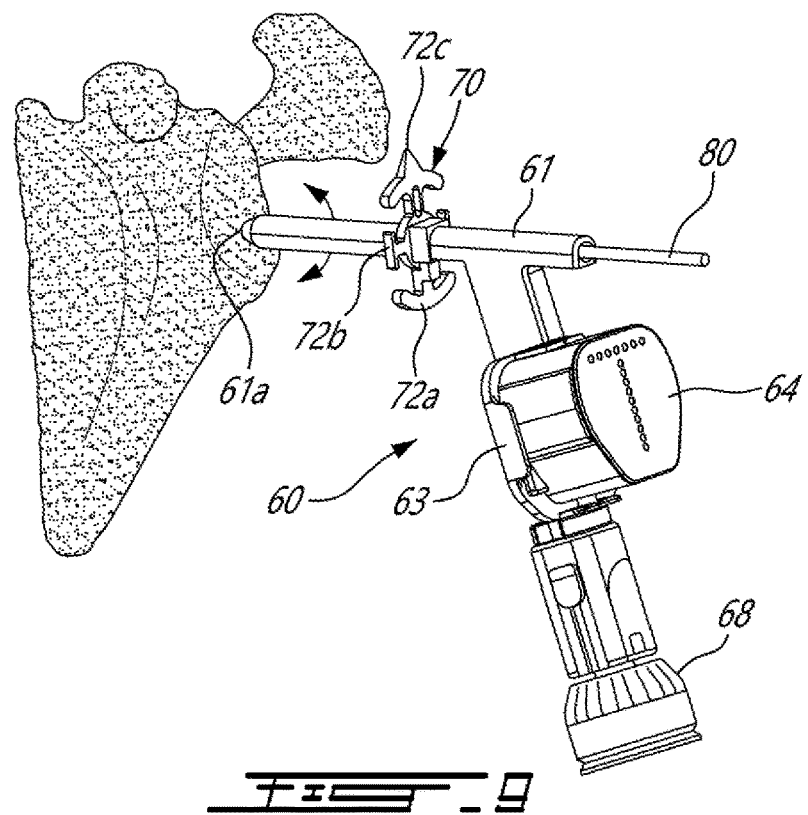
FIG. 9 is a perspective view of the glenoid navigation assembly of FIG. 7 with a registration interface being removed.

Once the appropriate location of the alignment member 72 is attained, an orientation of the pin 80, i.e., its trajectory, may be navigated. So as not to have the registration interface 70 interfere with the movement of the pin guide 60, the registration interface 70 may be slid away by moving same along the cannulated shaft 61, as shown in FIG. 9. In another embodiment, the registration interface 70 could simply be clipped off of the pin guide 60, in an embodiment without the translational DOF. From that point on, the inertial sensor unit 64 is used to achieve the proper orientation of the pin 80. As the inertial sensor unit 64 has been turned on and has been programmed with the inclination and version of the pin 80, for instance as pre-programmed using the GUI of FIG. 6, the inertial sensor unit 64 may provide guidance, for instance through LEDs thereon, to indicate when the pin 80 is properly oriented relative to the glenoid. To do so, a plane of the glenoid may have been determined based on the interaction between the registration interface 70 and the glenoid, during the positioning step. As the registration interface 70 is in a fixed orientation on the pin guide 60, an orientation of the glenoid may be set in the virtual coordinate system tracked by the inertial sensor unit 64 when the registration interface 70 is against the glenoid. A modelling of the scapula/glenoid, for instance pre-operative with any appropriate imaging modality, may be used to determine an orientation of the surface of the glenoid. Therefore, when the registration interface 70 is against the glenoid, as planned, and considering the fixed orientation of the registration interface 70 on the pin guide 60, the inertial sensor unit 64 may be calibrated or set with the orientation from the modelling. It is assumed that the scapula is fixed in space during these operations. It is however contemplated to provide an inertial sensor unit on the glenoid so as to monitor any movement. The shape of the end 61a may assist in preserving a position (x,y,z) of the shaft 61, for instance by having a rounded surface (e.g., hemispherical), contacting the glenoid, with an orientation (phi, theta and/or row) of the shaft 61 varies.

Figure 10:
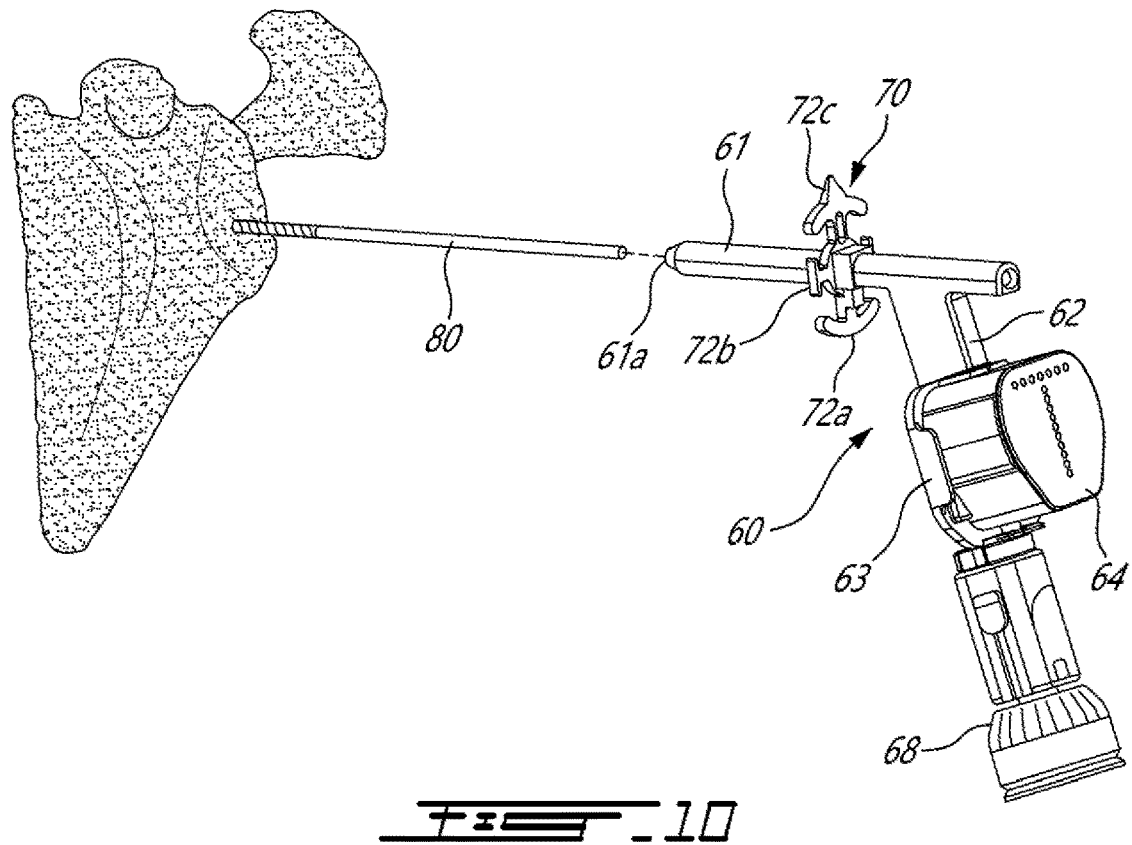
FIG. 10 is a perspective view of the glenoid navigation assembly as removed after the positioning of a guide pin in the glenoid.

The maneuvering of the pin guide 60 may be achieved by the robotic arm 100 of FIG. 11, in a collaborative mode with maneuvers of a user. The robotic arm 100 may preserve the position of the tip 61a of the cannulated shaft 61 against the glenoid and rotate a remainder of the pin guide 60. Once the desired orientation or trajectory for the pin 80 is achieved, the pin 80 may be screwed into the glenoid. As shown in FIG. 10, the pin guide 60 may then be slid off of the pin 80. The pin 80 will serve as a trajectory guide for a cannulated drill, for a reamer, for example. A location of the pin 80 may correspond to a location of a peg of an implant, such as a glenosphere, that will be implanted onto the glenoid.

The robotic arm 100 of FIG. 11 is an example of an arm that may be used with the with humerus cutting assembly 10 of FIG. 1 and/or the glenoid navigation assembly 50 of FIG. 7. In an embodiment, the assemblies 10/50 connected to an effector end of the robotic arm 100. The robotic arm 100 may provide 6 DOFs of movement to the effector end, though fewer or more may be possible. In an embodiment, the robotic arm 100 is used in a collaborative mode, as manipulated by a user, with the possibility to provide some movement constraints, such as preserving the position of pin 80 on the glenoid as described above. Alternatively, the arm may be a rapidly repositionable surgical support arm, such as the WalterLorenz® Surgical Assist Arm (Zimmer Biomet, Jacksonville, Florida), which allows for the user to navigate the position and orientation of the assemblies by hand but then lock the joints of the support arm once the desired position and orientation is attained according to the GUI of the respective inertial support units of the assemblies.

The robotic or rapidly repositionable support arm 100 of FIG. 11 may for example be as described in United States Patent Application Publication No. 2018/0116758, incorporated herein by reference. The robotic arm 100 may be referred to as a lockable support assembly that may have a base arm portion 101 having a lower end 101A and an upper end 101B, and a distal arm portion 102 having a proximal end 102A and a distal end 102B. A central joint 103 may be linking the upper end 101B of the base arm portion 101 to the proximal end 102A of the distal arm portion 102. For example, the central joint 103 is a rotational joint (e.g., one DOF revolute joint). A lower joint 104 may be at the lower end 101B of the base arm portion 101, and may serve to connect the robotic arm 100 to a structure, to a station, etc. The lower joint 104 may also be for instance a rotational joint, such as a spherical joint or universal joint (e.g., two or more rotational DOFs). In FIG. 11, the lower joint 104 is shown having a ball, with the proximal end 102A. An upper joint 105 may be at the distal end 102B of the distal arm portion 102. The upper joint 105 may also be for instance a rotational joint, such as a spherical joint or universal joint (e.g., two or more rotational DOFs). The effector end 106 of the robotic arm 100 may be at the upper joint 105, with the assemblies 10/50 connected to the effector end 106 of the robotic arm 100. A locking mechanism may be integrated inside the robotic arm 100 in the manner described in United States Patent Application Publication No. 2018/0116758, so as to selectively block movement of one or more of DOFs of the robotic arm 100. For instance, all of the DOFs of the robotic arm 100 may be locked by the locking mechanism, so as to block movement between the structure, the base arm portion 101, the distal arm portion 102, and the effector end 106. The locking mechanism may be coupled to the base arm portion 101 at a location above the lower joint 104 and configured to simultaneously deliver locking forces to the central joint 103, the lower joint 104, and to the upper joint 105. Moreover, the locking mechanism may increase or decrease a resistance at the various joints 103, 104, 105, for the user of the robotic arm 100 to experience variation of resistance in displacing the effector end 106, or arm portions. The joints 103, 104 and/or 105 may employ frictional forces to block movements, and a reduction in forces applied at a joint may reduce friction, and hence permit some movement, though with a resistance that may be proportional to the frictional forces. This may be used to guide the user in the manipulations.

In an embodiment, a controller 110 is provided to operate the robotic arm 100, for instance in conjunction with the assemblies 10/50. The controller 110 may be operatively connected to the robotic arm 100 and inertial sensor units 24, 34, and/or 64 via a wireless connection, or alternatively may be connected via wire or may be integral to the assemblies 10 and 50. For example, the controller 110 may be part of a computer-assisted surgery system, and may include a processor unit, and a non-transitory computer-readable memory communicatively coupled to the processor and computer-readable program instructions executable by the processor unit for operating the robotic arm 100. The controller 110 may operate a surgical flow based on the procedure being performed. Accordingly, various interfaces may be provided if necessary. This may include button 110A on the robotic arm 100, which button 110A may activate and/or deactivate the locking mechanism in the robotic arm 100. In an embodiment, the controller 110 receives signals from the inertial sensor unit 24, 34, and/or 64 to receive orientation information related to the assemblies 10 and 50. An inertial sensor unit 114 may optionally be provided on the robotic arm 100, such as at the effector end 106, or other location, to provide navigation data to the controller 110. The inertial sensor unit 114 may be integrated into the robotic arm 100, or may be an add-on pod, in the manner shown for the assemblies 10 and 50.

Consequently, the robotic arm 100 and controller 110 could be used in the surgical workflows related to the assemblies 10 and/or 50, or in other procedures. According to an embodiment, the robotic arm 100 may automatically lock by actuating its locking mechanism, once the robotic arm 100 has sensed that it has reached its desired orientation, for instance by the signals from the inertial sensor unit 114. The signals of the inertial sensor unit 114 may be used jointly with the data of other inertial sensor units (e.g., 24, 34, and/or 64) and may be with respect to the reference coordinate system in which the anatomical features are registered. The user could then unlock the robotic arm 100, for instance via the button 110A. Alternatively, the function of the button 110A may be reversed—the user may depress the button 110A during the surgical navigation, during which the robotic arm 100 is unlocked, and maintain the depressed state when the automatically locking occurs. In such an embodiment, releasing the button 110A would reset the automatically locking functionality and the arm 100 would remained locked until unlocked by the user, by, for example, double tapping the button 110A. After being unlocked the controller 110 would revert to a state where it monitors whether the robotic arm 100 has sensed that it has reached its desired orientation, i.e., sensing for an automatic lock or "auto lock".

Another contemplated feature of the robotic arm 100 and controller 110 would be an automatic locking when the inertial sensor unit 114 senses that the robotic arm 100 has not been moved around for a given period of time. The joint resistance may block the robotic arm 100, but the automatic lock would preclude any movement, such as movements due to gravity or accidental contact, for example.

It is contemplated to achieve some of these functions without any inertial sensor unit on the robotic arm 100. For example, the robotic arm 100 could be calibrated using the inertial sensor units on the assemblies 10 and/or 50, and additional data such as a pre-operative plan. For example, a single inertial sensor unit could be used in humeral resection to align the robotic arm 100 with the humeral axis, with such an orientation being recorded as a "0" reference, and then match version and inclination based on the "0" reference. Encoders or like joint sensors in the robotic arm 100 may be coupled to the controller 110 to navigate the robotic arm 100 after such a calibration.

In accordance with an embodiment, a reference location is established on the bone or like anatomical landmark. The robotic arm 100 with inertial sensor unit 114 is calibrated while locked at the reference location. Navigation may be initiated, for instance by triggering the inertial sensor unit 114. Thus, live navigation begins on the inertial sensor unit 114 and/or interface of the controller 110. The "auto lock" or "auto block" feature may be deployed through live navigation, as the sensing on the inertial sensor unit 114 monitors the orientation of the robotic arm 100. To move the robotic arm 100, it may be required that the user press the button 110A to unlock the locking mechanism in the robotic arm 100 and enable a repositioning of the instrument at the effector end 106, for instance to a target orientation/location. It may be required that the button 110A be depressed and held to maintain the arm 100 in the unlocked state, though a single discrete press of the button 110A could put the robotic arm 100 in a collaborative mode. Various features may be programmed during navigation. When the controller 110 determines that the target orientation has been achieved and held for a predefined period of time, the robotic arm 100 may be forced to "auto lock." When the button 110A is still depressed, the "auto lock" may still occur, and a release of the button 110A may reset the "auto lock" functionality. As additional programmable feature, a standard double tap press on the button 110A or other parts of the robotic arm 100 would unlock the robotic arm and/or initiate the "auto lock" sensing again, for instance for a further step of the surgical workflow. This would enable for instance a user to move the robotic arm 110 out of the way, with the possibility of navigating back to the target orientation for "auto lock" again. The "auto lock" sensing feature may be programmed to end when the inertial sensor unit 114 is unclipped/turned off or the navigation application is no longer running on the controller 110.

In accordance with another embodiment, the robotic arm 100 could be used to support retractors. The controller 110 may operate an auto release function, in which the robotic arm 100 releases the lock temporarily. This may occur for example in the event that the inertial sensor unit 114 detects an unexpected motion/forces on the robotic arm 100. As yet another embodiment, the robotic arm 100 may vary the friction in the joints, so as to cause a reduced/force or 'drag', or an increase thereof. For example, this may occur when the robotic arm 100 is used to manipulate the cutting guide 30, as the inertial sensor unit 34 indicates to the controller 110 that the target orientation is nearing.

The embodiments of the humerus cutting assembly 10 of FIG. 1 and/or of the glenoid navigation assembly 50 of FIG. 7 provided above are described with reference to inertial sensor tracking (e.g., accelerometers), but other tracking technologies are contemplated.

The humerus cutting assembly 10 of FIG. 1 may be programmed in such a way that it defines a system for guiding an alteration to a head of a humerus, with the processing unit associated with the inertial sensor unit(s) 24 and/or 34. The system may thus perform any of setting a reference orientation of a humerus when an assembly featuring a guide is attached to the humerus in a predetermined manner, obtaining an output as an orientation of the guide relative to the humerus is varied, tracking a current orientation of the humerus relative to the reference orientation using the output, and/or calculating and outputting an inclination angle and/or a retroversion angle as a function of the current orientation of the guide, the inclination angle and/or a version angle being indicative of an alteration to the head of the humerus associated to the current orientation of the guide.

The glenoid navigation assembly 50 of FIG. 7 may be programmed in such a way that it defines a system for guiding an alteration to a glenoid, with the processor unit associated with the inertial sensor unit 64. The system may thus perform any of setting a reference orientation of a glenoid when an assembly featuring a guide is applied against the glenoid in a predetermined manner, obtaining an output as an orientation of the guide relative to the glenoid is varied, tracking a current orientation of the guide relative to the reference orientation using the output, and calculating and outputting an inclination angle and/or a version angle as a function of the current orientation of the guide, the inclination angle and/or a version angle being indicative of an alteration to the glenoid associated to the current orientation of the guide.

EXAMPLES

The following examples can each stand on their own, or can be combined in different permutations, combinations, with one or more of other examples.

Example 1 is a humerus cutting assembly comprising: a guide frame having an attachment member adapted to be secured to a humerus adjacent to a humeral head, and a cutting guide releasably connected to the guide frame, the cutting guide configured to guide a tool in altering the humeral head; at least one inertial sensor unit on the cutting guide, the inertial sensor unit tracking an orientation of the cutting guide relative to the humerus based on the releasable connection between the cutting guide and the guide frame.

In Example 2, the subject matter of Example 1 includes, wherein the attachment member includes a plate configured to be applied against the humerus.

In Example 3, the subject matter of Example 2 includes, wherein the attachment member includes at least one fastener to secure the plate to the humerus.

In Example 4, the subject matter of Examples 2-3 includes, wherein the plate includes at least one patient-specific surface being a negative of a corresponding surface of the humerus.

In Example 5, the subject matter of Examples 1-4 includes, wherein the guide frame has an elongated arm configured to be connected to a portion of an arm of the humerus, away from the humerus.

In Example 6, the subject matter of Example 5, including a clamp at an end of the elongated arm configured to be connected to the portion of the arm of the humerus.

In Example 7, the subject matter of Example 6 includes, wherein the clamp has biased jaws.

In Example 8, the subject matter of Examples 5-7 includes, wherein the elongated arm defines a joint with at least one translational degree of freedom.

In Example 9, the subject matter of Example 8 includes, wherein the joint with at least one translational degree of freedom is a lockable telescopic joint.

In Example 10, the subject matter of Examples 5-9, including a support for the at least one inertial sensor unit on the elongated arm.

In Example 11, the subject matter of Examples 5-10, including a side arm projecting from the elongated arm, the plate being at an end of the side arm.

In Example 12, the subject matter of Examples 1-11 includes, wherein the side arm defines a side-arm joint with at least one translational degree of freedom.

In Example 13, the subject matter of Example 12 includes, wherein the side-arm joint with at least one translational degree of freedom is a lockable telescopic joint.

In Example 14, the subject matter of Examples 1-13, including a support for releasably receiving the at least one inertial sensor unit on the cutting guide.

In Example 15, the subject matter of Example 14 includes, wherein the support is on an arm projecting from a remainder of the cutting guide, a coupler being at an end of the arm.

In Example 16, the subject matter of Examples 1-15 includes, wherein the cutting guide has at least one cut slot, and holes for receiving fasteners to secure the cutting guide to the humerus.

In Example 17, the subject matter of Examples 1-16 includes, wherein the releasable connection is a male-female coupling between the guide frame and the cutting guide, the male-female coupling defining a unique coupling orientation.

Example 18 is a system for guiding an alteration to a head of a humerus comprising: a processor unit, and a non-transitory computer-readable memory communicatively coupled to the processor and comprising computer-readable program instructions executable by the processor unit for: setting a reference orientation of a humerus when an assembly featuring a cutting guide is attached to the humerus in a given orientation, obtaining an output from at least one inertial sensor on the cutting guide as an orientation of the cutting guide relative to the humerus is varied, tracking a current orientation of the humerus relative to the reference orientation using the output, and calculating and outputting at least one angle being indicative of an alteration to the head of the humerus associated to the current orientation of the cutting guide.

In Example 19, the subject matter of Example 18 includes, wherein setting the reference orientation includes setting the reference orientation when the cutting guide is coupled to a guide frame mounted to the humerus.

In Example 20, the subject matter of Example 19 includes, wherein setting the reference orientation includes setting the reference orientation with the at least one inertial sensor on the guide frame.

In Example 21, the subject matter of Example 20 including tracking the at least one inertial sensor on the guide frame being detached from the guide frame and connected to the cutting guide, after the setting.

In Example 22, the subject matter of Examples 19-21 further including obtaining the output from the at least one inertial sensor on the cutting guide includes obtaining an output from another inertial sensor on the guide frame.

In Example 23, the subject matter of Example 22 includes, wherein tracking the current orientation of the humerus relative to the reference orientation includes using the output of the inertial sensor on the cutting guide and the output of the inertial sensor on the guide frame.

In Example 24, the subject matter of Examples 18-23 includes, wherein calculating and outputting at least one angle includes calculating and outputting the inclination angle and/or the retroversion angle as a function of the current orientation of the cutting guide.

Example 25 is a glenoid navigation assembly comprising: a pin guide having a cannulated shaft, the cannulated shaft adapted to receive a guide pin therein; a registration interface at the end of the cannulated shaft and configured for abutting a glenoid, the registration interface having at least one visual alignment member for visually assisting in a positioning of the guide pin on the glenoid; and at least one inertial sensor unit on the glenoid navigation assembly, the inertial sensor unit tracking an orientation of the cannulated shaft relative to the glenoid based on a contact between the registration interface and the glenoid surface.

In Example 26, the subject matter of Example 25 includes, wherein the at least one alignment member includes a pair of spaced apart members indicative of a size of the glenoid.

In Example 27, the subject matter of Examples 25-26 includes, wherein the at least one alignment member includes a member configured to abut against a rim of the glenoid.

In Example 28, the subject matter of Examples 25-27 includes, wherein the at least one alignment member includes a pointer configured to point to a landmark of the glenoid.

In Example 29, the subject matter of Examples 25-28 includes, wherein the registration interface is patient specific, wherein the at least one alignment member is based on patient imaging.

In Example 30, the subject matter of Examples 25-29 includes, wherein a translational joint is formed between the registration interface and the cannulated shaft, for the registration interface to be movable along the cannulated shaft.

In Example 31, the subject matter of Examples 25-30 includes, wherein the cannulated shaft has a tapered end configured to be in contact with the glenoid.

In Example 32, the subject matter of Examples 25-31 includes, wherein an end of the cannulated shaft is rounded, the end configured to be in contact with the glenoid.

In Example 33, the subject matter of Examples 25-32 includes, wherein the at least one inertial sensor unit is secured to a handle projecting from the cannulated shaft.

In Example 34, the subject matter of Example 33, including a support for releasably receiving the at least one inertial sensor unit on the handle.

In Example 35, the subject matter of Example 34, including a robot arm coupler on the handle.

Example 36 is a system for guiding an alteration to a glenoid comprising: a processor unit, and a non-transitory computer-readable memory communicatively coupled to the processor and comprising computer-readable program instructions executable by the processor unit for: setting a reference orientation of a glenoid when an assembly featuring a guide is applied against the glenoid at a given position, obtaining an output from an inertial sensor on the guide as an orientation of the guide relative to the glenoid is varied, tracking a current orientation of the guide relative to the reference orientation using the output, and calculating and outputting an angle, the angle being indicative of an alteration to the glenoid associated to the current orientation of the guide.

In Example 37, the subject matter of Example 36 includes, wherein setting the reference orientation includes setting the reference orientation when a registration interface positions the guide against the glenoid in the given position.

In Example 38, the subject matter of Examples 36-37 includes, wherein the guide is a cannulated shaft, and wherein obtaining the output from the inertial sensor on the guide includes obtaining the output as the cannulated shaft is rotated relative to the given position.

In Example 39, the subject matter of Examples 36-38 includes, wherein calculating and outputting an angle includes calculating and outputting an inclination angle and/or a version angle as a function of the current orientation of the guide.

Example 40 is a system for guiding an alteration to a head of a humerus comprising: a processor unit, and a non-transitory computer-readable memory communicatively coupled to the processor and comprising computer-readable program instructions executable by the processor unit for: setting a reference orientation of a humerus when an assembly featuring a cutting guide is attached to the humerus in a predetermined manner, robotically manipulating the guide relative to the humerus with a robotic arm, obtaining an output representative of a current orientation of the guide as the guide is robotically manipulated, tracking a current orientation of the humerus relative to the reference orientation using the output, calculating and outputting at least one angle being indicative of an alteration to the head of the humerus associated to the current orientation of the cutting guide, and auto-blocking the robotic arm when a desired value for the angle is reached.

In Example 41, the subject matter of Example 40 includes, wherein setting the reference orientation includes setting the reference orientation when the guide is coupled to a guide frame mounted to the humerus.

In Example 42, the subject matter of Example 41 includes, wherein setting the reference orientation includes setting the reference orientation with the at least one inertial sensor on the guide frame.

In Example 43, the subject matter of Examples 42 including tracking the at least one inertial sensor on the guide frame being detached from the guide frame and connected to the guide, after the setting.

In Example 44, the subject matter of Examples 41-43 further including obtaining the output from the at least one inertial sensor on the guide includes obtaining an output from another inertial sensor on the guide frame.

In Example 45, the subject matter of Example 44 includes, wherein tracking the current orientation of the humerus relative to the reference orientation includes using the output of the inertial sensor on the guide and the output of the inertial sensor on the guide frame.

In Example 46, the subject matter of Examples 40-45 includes, wherein calculating and outputting at least one angle includes calculating and outputting the inclination angle and/or the retroversion angle as a function of the current orientation of the cutting guide.

In Example 47, the subject matter of Example 46 includes, wherein auto-blocking the robotic arm when a desired value of the angle is reached includes auto-blocking the robotic arm when the inclination angle and/or the retroversion angle is/are reached.

In Example 48, the subject matter of Examples 40-47 includes, wherein auto-blocking the robotic arm when a desired value for the angle is reached includes increasing a frictional force in the robotic arm as the robotic arm approaches the desired value.

In Example 49, the subject matter of Examples 40-48 includes, wherein auto-blocking the robotic arm when a desired value for the angle is reached includes auto-blocking when a detent on the robotic arm is being depressed.

In Example 50, the subject matter of Example 49, including releasing the robotic arm from the auto-blocking as a response to an action on the detent.

Example 51 is a system for guiding an alteration to a glenoid comprising: a processor unit, and a non-transitory computer-readable memory communicatively coupled to the processor and comprising computer-readable program instructions executable by the processor unit for: setting a reference orientation of a glenoid when an assembly featuring a guide is applied against the glenoid in a given position, robotically manipulating the guide relative to the glenoid with a robotic arm, obtaining an output representative of a current orientation of the guide as the guide is robotically manipulated, tracking a current orientation of the guide relative to the reference orientation using the output, calculating and outputting at least one angle being indicative of an alteration to the glenoid associated to the current orientation of the guide, and auto-blocking the robotic arm when a desired value for the angle is reached.

In Example 52, the subject matter of Example 51 includes system according to claim 51, wherein setting the reference orientation includes setting the reference orientation when a registration interface positions the guide against the glenoid in the given position.

In Example 53, the subject matter of Examples 51-52 includes, wherein the guide is a cannulated shaft, and wherein obtaining the output from the inertial sensor on the guide includes obtaining the output as the cannulated shaft is rotated relative to the given position by the robotic arm.

In Example 54, the subject matter of Examples 51-53 includes, wherein calculating and outputting an angle includes calculating and outputting an inclination angle and/or a version angle as a function of the current orientation of the guide.

In Example 55, the subject matter of Example 54 includes, wherein auto-blocking the robotic arm includes auto-blocking the robotic arm when the desired inclination angle and/or the version angle is/are reached.

In Example 56, the subject matter of Examples 51-55 includes, wherein auto-blocking the robotic arm when a desired value for the angle is reached includes increasing a frictional force in the robotic arm as the robotic arm approaches the desired value.

In Example 57, the subject matter of Examples 51-56 includes, wherein auto-blocking the robotic arm when a desired value for the angle is reached includes auto-blocking when a detent on the robotic arm is being depressed.

In Example 58, the subject matter of Example 57 including releasing the robotic arm from the auto-blocking as a response to an action on the detent.

The invention claimed is:

1. A humerus cutting assembly comprising:
   a guide frame having an attachment member adapted to be secured to a humerus adjacent to a humeral head, and
   a cutting guide releasably connected to the guide frame, the cutting guide configured to guide a tool in altering the humeral head;
   at least one inertial sensor unit on the cutting guide, the inertial sensor unit tracking an orientation of the cutting guide relative to the humerus based on a releasable connection between the cutting guide and the guide frame.

2. The humerus cutting assembly according to claim 1, wherein the attachment member includes a plate configured to be applied against the humerus.

3. The humerus cutting assembly according to claim 2, wherein the attachment member includes at least one fastener to secure the plate to the humerus.

4. The humerus cutting assembly according to claim 2, wherein the plate includes at least one patient-specific surface being a negative of a corresponding surface of the humerus.

5. The humerus cutting assembly according to claim 1, wherein the guide frame has an elongated arm configured to be connected to a portion of an arm of the humerus, away from the humerus.

6. The humerus cutting assembly according to claim 5, including a clamp at an end of the elongated arm configured to be connected to the portion of the arm of the humerus.

7. The humerus cutting assembly according to claim 6, wherein the clamp has biased jaws.

8. The humerus cutting assembly according to claim 5, wherein the elongated arm defines a joint with at least one translational degree of freedom.

9. The humerus cutting assembly according to claim 8, wherein the joint with at least one translational degree of freedom is a lockable telescopic joint.

10. The humerus cutting assembly according to claim 5, including a support for the at least one inertial sensor unit on the elongated arm.

11. The humerus cutting assembly according to claim 5, including a side arm projecting from the elongated arm, the plate being at an end of the side arm.

12. The humerus cutting assembly according to claim 11, wherein the side arm defines a side-arm joint with at least one translational degree of freedom.

13. The humerus cutting assembly according to claim 12, wherein the side-arm joint with at least one translational degree of freedom is a lockable telescopic joint.

14. The humerus cutting assembly according to claim 1, including a support for releasably receiving the at least one inertial sensor unit on the cutting guide.

15. The humerus cutting assembly according to claim 14, wherein the support is on an arm projecting from a remainder of the cutting guide, a coupler being at an end of the arm.

16. The humerus cutting assembly according to claim 1, wherein the cutting guide has at least one cut slot, and holes for receiving fasteners to secure the cutting guide to the humerus.

17. The humerus cutting assembly according to claim 1, wherein the releasable connection is a male-female coupling between the guide frame and the cutting guide, the male-female coupling defining a unique coupling orientation.

\* \* \* \* \*